United States Patent [19]

Tournier et al.

[11] Patent Number: 5,370,901

[45] Date of Patent: Dec. 6, 1994

[54] COMPOSITIONS FOR INCREASING THE IMAGE CONTRAST IN DIAGNOSTIC INVESTIGATIONS OF THE DIGESTIVE TRACT OF PATIENTS

[75] Inventors: Herve Tournier, Valleiry; Roland Hyacinthe, Douvaine, both of France; Friedrich Cavagna, Vicenza, Italy

[73] Assignee: Bracco International B.V., Amsterdam, Netherlands

[21] Appl. No.: 824,311

[22] Filed: Jan. 23, 1992

[30] Foreign Application Priority Data

Feb. 15, 1991 [EP] European Pat. Off. ........ 91810105.6

[51] Int. Cl.⁵ .................. A61K 9/16; A61K 49/00; A61B 8/12
[52] U.S. Cl. .................. 427/2.12; 427/2.14; 424/9; 436/173; 128/653.4; 128/660.1
[58] Field of Search .................. 427/2, 3; 424/4, 9, 424/78.01; 436/173, 806; 128/653.1, 653.4, 654, 660.01

[56] References Cited

U.S. PATENT DOCUMENTS

| | | | |
|---|---|---|---|
| 4,729,892 | 3/1988 | Beall | 424/9 |
| 4,795,698 | 1/1989 | Owen et al. | 427/2 |
| 4,822,594 | 4/1989 | Gibby | 436/173 |
| 4,863,717 | 9/1989 | Keana | 436/173 |
| 4,927,624 | 5/1990 | Bryant et al. | 424/9 |
| 5,154,914 | 10/1992 | Elgavish et al. | 436/173 |
| 5,182,370 | 1/1993 | Felder et al. | 534/15 |
| 5,205,287 | 4/1993 | Erbel et al. | 128/660.01 |
| 5,208,324 | 5/1993 | Klaveness et al. | 426/173 |
| 5,215,680 | 6/1993 | D'Arrigo | 436/173 |
| 5,236,694 | 8/1993 | Antich et al. | 128/653.4 |
| 5,260,050 | 11/1993 | Ranney | 436/173 |
| 5,281,408 | 1/1994 | Unger | 128/654 |
| 5,302,372 | 4/1994 | Lin et al. | 128/660.01 |

FOREIGN PATENT DOCUMENTS

| | | |
|---|---|---|
| 275215 | 7/1988 | European Pat. Off. . |
| 299910 | 1/1989 | European Pat. Off. . |
| 409351 | 1/1991 | European Pat. Off. . |
| 3908623 | 9/1990 | Germany . |
| 8800060 | 1/1988 | WIPO . |

*Primary Examiner*—Shrive Beck
*Assistant Examiner*—Diana Dudash
*Attorney, Agent, or Firm*—Nixon & Vanderhye

[57] ABSTRACT

Method of making an ingestible composition useful as a contrast enhancing agent in ultrasonic imaging of the digestive tract of humans and animals, wherein the composition has microballoons as contrast enhancing particles bound to an organic carrier phase, which when hydrated has an adhesive affinity for the gastrointestinal mucosa.

Method includes grafting a silane coupler having at least two reactive functions to the microballoons through one of the reactive functions and binding the grafted microballoons to the carrier phase through another reactive function.

3 Claims, 3 Drawing Sheets

COMPOSITIONS FOR INCREASING THE IMAGE CONTRAST IN DIAGNOSTIC INVESTIGATIONS OF THE DIGESTIVE TRACT OF PATIENTS

BACKGROUND OF THE INVENTION

The present invention concerns innocuous ingestible or enterally administrable compositions which, depending on the contrast agent incorporated thereto, can be used as contrast enhancer media for imaging, on the first hand in ultrasonic echography, and on the second hand, in nuclear magnetic resonance imaging (NMRI), both of the gastro-intestinal tract of animal and human patients.

It is well known that echography and NMRI are investigative diagnosis techniques which enable the direct electronic visualization of internal organs in living beings and are therefore powerful help and guide in prognosis, medical treatment and surgery. These techniques can often advantageously supplement or replace X-ray tomography as well as the use of radio-active tracer compounds which may have obvious undesirable side-effects.

It is also well known that contrast echography relies on the administration to patients of dispersions or suspensions of microbodies containing air or a gas, in a medium, and thereafter applying ultrasonic waves which become reflected by said microbodies to provide desired echographic signals. In this connection, it has been recognized that air or gas-filled microspheres, e.g. microbubbles or microballoons, suspended in a liquid are exceptionally efficient ultrasound reflectors for echography. In this disclosure the term of "microbubble" specifically designates air or gas globules in suspension in a liquid which generally results from the introduction therein of air or a gas in divided form, the liquid preferably also containing surfactants or tensides to control the surface properties and the stability of the bubbles. The term of "microcapsule" or "microballoon" designates preferably air or gas bodies with a material boundary or envelope, e.g. a polymer membrane wall. Both microbubbles and microballoons are useful as ultrasonic contrast agents. For instance injecting into the bloodstream of living bodies suspensions of gas microbubbles or microballoons (in the range of 0.5 to 10 $\mu$m) in a carrier liquid will strongly reinforce ultrasonic echography imaging, thus aiding in the visualization of internal organs. Imaging of vessels and internal organs can strongly help in medical diagnosis, for instance for the detection of cardiovascular and other diseases.

It is also well known that NMRI techniques comprise subjecting a patent to a main static magnetic field combined with a linear gradient magnetic field, both being directed to some parts of the body to be investigated. The magnetic fields act on the nuclei of atoms with fractional spin quantum numbers and encode them into various degrees of statistical alignment with different resonant frequencies in a selected direction of orientation; the nuclei of concern here are mainly that of hydrogen atoms, i.e. protons, these being predominantly that of molecules present in relatively high concentration in or around the organs to be investigated, viz, the protons of water and lipids. For doing the measurements, one will apply to the parts of the body under investigation pulses of radio-frequency that matches with the resonance energy of the protons involved in the tissues or fluids of said parts of the body. When the protons under consideration are excited by a pulse of resonant energy, they are raised to a higher energy state which causes them to flip from the average orientation direction controlled by the magnetic field. Thereafter, the protons will return to their original state by relaxation in an exponential time dependent fashion, the corresponding energy then reemitted (spin-echo) forming a response signal typical of the protons under consideration, i.e. depending on their immediate environment.

NMRI techniques are actually based on the detecting, acquiring and electronically processing of this signal (according to Fourier transforms) and thereafter displaying it spatially on a screen, thus forming an image whose various patterns correspond to areas having protons in different environments, i.e. to protons belonging to organ tissues or body fluids being subjected to investigation.

Among the critical factors pertaining to MRI, one usually distinguishes two mutually perpendicular components of the proton-distinctive relaxation time parameter, namely the spin-lattice component along the axis of magnetization (called $T_1$), which corresponds to the release of energy to the nuclear environment, and The perpendicular or transverse (spin-spin) relaxation component (called $T_2$), that corresponds to the returning of the nucleus to the initial statistical energy level. Either $T_1$ or $T_2$ can contribute to the definition of the NMR images depending on the kind of organ selected and the measurement conditions.

It should be noted that when the measurements are carried out in the absence of agents added for increasing image contrasts, the differences in relaxation time constants between protons in various parts of the organs are small and the image is of poor to bad quality. The contrast effect can however be enhanced by the presence, in the environment of the hydrated molecules under excitation, of a variety of magnetic species, e.g. paramagnetic (which mainly affect $T_1$) and ferromagnetic or superparamagnetic (which mainly affect the $T_2$ response). The paramagnetic substances include some metals in the ionic or organo-metallic state (e.g. $Fe^{+3}$, $Mn^{+2}$, $Gd^{+3}$ and the like, particularly in the form of chelates to decrease the intrinsic toxicity of the free metal ions). Ferromagnetic contrast substances preferably include magnetic aggregate particles of micronic or submicronic size, i.e. not smaller than about 100–200 nm, for instance particles of magnetite ($Fe_3O_4$), $\gamma$-$Fe_2O_3$, ferrites and other magnetic mineral compounds of transition elements. Superparamagnetic materials are usually very small magnetic particles (below about 100–150 nm) which, because their size is under a critical value, do not behave any longer as small autonomous magnets, i.e they will align in a preferential direction only when subjected to an external magnetic field. The advantage of the superparamagnetic materials (also defined sometimes as superparamagnetic fluids) over the ferromagnetic particles is mainly of efficiency density, i.e. being smaller, the number of available magnetic particles for a given weight of metal is greater in the case of superparamagnetic particles than with ferromagnetic particles and the magnetic efficiency on the neighboring protons is further enhanced.

For ultrasonic or NMRI imaging of the digestive tract, the particulate contrast agents, whether in the form of gas-filled microspheres or particles of ferromagnetic, superparamagnetic, or paramagnetic materials, are usually administered orally or rectally, either neat or preferably with a carrier.

For instance, EP-A-275.215 (AMERSHAM) discloses NMRI contrast enhancers for the investigation of the digestive tract comprising complexes of paramagnetic metal species like gadolinium, iron, manganese and the like associated with mineral particulate carriers such as alkaline-earth polyphosphates and apatite.

EP-A-83.760=WO85/05534 (AMERSHAM) discloses EDTA, DTPA and NTA chelates of paramagnetic metals chemically bonded to organic polymer carriers such as sepharose, dextran, dextrin, starch and the like.

Also in EP-A-299.920 (SCHERING), there are disclosed complexes between paramagnetic metals such as Cr, Mn, Fe, Ni, Co, Gd, etc. and polysulfated oligosaccharides like sucrose or maltose, these complexes being used for NMRI of the digestive tract.

It has been indicated above that paramagnetic contrast agents in which the metals are in the ionic state or in the form of metal-organic compounds are often metabolizable and toxic and, although this toxicity can be controlled to some extent by using very strong chelatants and non-metabolizable polymer carriers, it is desirable to further minimize possible hazards by using less toxic materials, e.g- non-metabolizable magnetic particles of sufficient size not to diffuse through the intestinal membrane; the micronic ferromagnetic and nanometric superparamagnetic aggregate particles typically fulfill such requirements. For instance, in U.S. Pat. No. 4,770,183 (ADVANCED MAGNETICS), there is recommended to use biodegradable sub-micron sized superparamagnetic metal oxide particles (1–50 nm) which may be used uncoated or coated with a polysaccharide (like dextran) or serum albumin. Coating is effected by precipitating the particles with alkali, starting with water solutions of metal salts in the presence of the polymer. These products are suitable for intravenous applications as well as for gastrointestinal applications, in which case they are administrable by intubation or enema, presumably because otherwise biodegradation by the stomach fluids would be too fast and toxicity might become a problem.

In WO85/04330 (NYCOMED), there is disclosed the use of ferromagnetic particles as contrast agents for NMRI. As mentioned before, ferromagnetic particles are bigger than superparamagnetic particles and behave as small permanent magnets which also achieve a significant reduction of $T_2$. For direct administration into the digestive tract, the ferromagnetic particles are preferably embedded in a cellulose matrix or coated with this matrix. Cellulose derivatives can also be added as viscosants but the reference indicates that contrast enhancement is not readily achieved beyond the stomach, presumably because the embedding cellulose matrix does not protect sufficiently the particles from attack by the stomach fluids. Non-biodegradable embedding or coating matrices are therefore recommended to minimize absorption of toxic materials by the body.

EP-A-186.616 (SCHERING) discloses the use of complexes of particles of magnetite ($Fe_3O_4$), γ-iron oxide ($Fe_2O_3$) and metal ferrites as contrast agents for NMRI. The cited complexants include oligo- and polysaccharides, proteins, polycarboxylic acids, protective colloids and other compounds- Examples of such compounds comprise polyvinyl-alcohol (PVA), polysilanes, polyethylene-imine, dextran, dextrin, oleic acid, gelatin, globulin, albumin, insulin, peptides and antibodies. The particles can also be encapsulated in liposomes. For enteral administration, the contrast agents are suspended in a water medium which may contain further ingredients such as salt or excipients like methylcellulose, viscosants, lactose, mannitol and surfactants like lecithin, Tween ®, Myrj ® and the like.

For enteral use, this document particularly mentions compositions containing dextrin- or dextran-magnetite complexes, the manufacturing of which is disclosed in U.S. Pat. No. 4,101,435 (MEITO SANGYO).

There is also reported by J. KLAVENESS et al, in Diagnostic Imaging International, November 1988, p. 70, the use as contrast agents #or the gastro-intestinal system of microspheres (3.5 μm) of sulfonated ion-exchange styrene-divinylbenzene resin coated with magnetite $Fe_3O_4$. The matrix is non-biodegradable and the particles with an iron content of about 20% are stable in the gastro-intestinal tract.

After testing the compositions of the cited prior art consisting of coated or uncoated magnetic particles in admixtures with polymer carriers, the present inventors noted that the contrast effect in NMR imaging is generally unstable and rapidly vanishes, presumably because despite the presence of the carrier phase the magnetic particles tend to coalesce or coacervate together under the influence of the external magnetic field which strongly reduces their controlling effect on the spin-relaxation of the neighbouring protons. They however also found that such undesirable coalescence of the magnetic particles and vanishing of the $T_2$ relaxing effect can be prevented by either selecting as the carrier phase substantially water-insoluble hydrophilic water-swelling substrates which tend to form gels with water or, when using water-soluble polymer carriers, raising the pH of the aqueous medium containing the magnetic particles to at least 13 when admixing with the polymer solution, and keeping the dry weight ratio of said polymers to magnetic particles not below 5:1 and, preferably, in the range of 100:1–10:1.

Although the exact reason of these findings is not definitely explained, it can be postulated that using carrier matrices which form nearly insoluble gels upon admixing with water (thixotropic or pseudo-plastic solutions) will locally raise the viscosity at the particle/-carrier interface to such extent that the particle mobility is impeded and agglomeration is prevented.

DESCRIPTION OF THE INVENTION

The present inventors also found that for efficient and selective imaging of portions of the digestive tract, it is advantageous to select carrier phases that have essential particular selective affinity for the gastric mucosa, e.g. carrier phases which can form intestinal linings or coatings on all or selected portions of the internal lumen surfaces. Hence when the carrier phase has special affinity for the gastric and intestinal mucosa, it will tend to stay in immobilized layer form thereon, thus further reducing particle mobility and preventing coalescence. Similar considerations pertain to the incorporation into the carrier phase of echogenic particles, e.g. air or gas-filled microspheres which, upon application of ultrasonic waves, will generate a reflected signal which permits visualizing by echography selected portions of the digestive tract or bladder.

The foregoing findings form the basis of the present invention as recited below and in the annexed claims, i.e. the invention mainly concerns diagnostic compositions to be used as contrast enhancing agents, on a first hand in the imaging by echography, and on a second hand in the NMR imaging, of portions of the digestive tract of humans and animals, said compositions comprising, depending on the needs, i.e. on the kind of investigation, at least one member of a group consisting of two types of contrast enhancing particles, viz. magnetically and ultrasonically responsive particles, in admixture with, or chemically bonded to, at least one physiologically acceptable carrier phase The said carrier phase is substantially water insoluble, although swellable by hydration and gel forming, and, when hydrated, has differential affinity for the gastro-intestinal mucosa, i.e. it adheres preferably to some areas thereof, thus forming luminal linings or coatings having specific magnetic contrast response patterns which enable improved visualization of specific portions of the oeso-gastro-duodenal tract.

The carrier phase of the present composition can be selected from water-soluble polymers which can form homogeneous solutions in aqueous media, in which case the proportion of signal generating particles therein preferably not exceeds 10% by weight of solution, more preferable 5%, for optimalized stability against coalescence when subjected to a steady magnetic field. The polymers which are convenient are for instance dextran, polyvinyl-pyrrolidone (PVP), carboxymethyl-cellulose (CMC) and the like. It is quite surprising that, contrary to products of the prior art with a high particle/carrier weight ratio, homogeneous dispersion of magnetic particles in relatively low concentrations in the carrier polymer remain stable in a magnetic field with virtually no or very little agglomeration of the magnetic particles, and hence no substantial weakening of the imaging response under the conditions of NMR imaging. Although the compositions with water-soluble polymers have no recognized specific affinity for the internal mucosa membrane of the digestive tract, they are useful for controlling the transit therethrough of the magnetic particles, either alone or when preferably used in association with bioadhesive carrier phases.

Carrier phases having affinity for the membrane mucosa of the digestive tract (bioadhesive carriers) can include most luminal coating materials in use for treatment, protection of medication of gastro-intestinal regions including, for instance, adhesives containing bismuth oxide, aluminum oxide and various clays such as montmorillonite and attapulgite designed for luminal applications. These materials also include cross-linked polymers such as polysiloxanes (Dimethicone ®), magnesium and other metals alginates, bioadhesive pectins and carbohydrates polysubstituted with groups such as sulfate, phosphate, sulfonate and phosphonate. One convenient polysulfated carbohydrate is sucrose octasulfate (also named sucralfate). It is already known that montmorillonite clays of the Beidel type can themselves function as useful contrast agents in the NMRI of the digestive tract of humans and animals, this being possibly due to some inherent magnetic properties of the montmorillonites. The contrast effect of Beidel montmorillonite clays is further enhanced when used as a carrier according to the invention.

These carriers have the general property to get hydrated with water and form therewith substantially insoluble gels which strongly adhere to the membrane mucosa. Depending on the selected carrier phase, the compositions of the invention can be made to have controllable transit time through the gastrointestinal tract and particular adhesion to selected portions thereof, thus enabling efficient NMRI of selected organs. Normally, the compositions using polymer carriers having no or little bioadhesion will permit faster transit than the compositions using carriers with strong bioadhesive character, hence controlled transit can be achieved with compositions in which non-bioadhesive and bioadhesive carriers are admixed in suitable proportions. It has also been surprisingly found that the particular selection of carriers used in the compositions of the invention, i.e. the carriers with enhanced affinity for mucosa membranes at low pH and/or soluble carriers with high dispersive capacity for magnetic particles, provide generally excellent transverse and longitudinal luminal imaging homogeneity.

One preferred type of bioadhesive polymers to be used as the carrier phase in this invention is a polymer or copolymer of acrylic acid containing a proportion of other monomers (generally di- or polyfunctional allyl ethers or acrylates) to impart a degree oil water-insolubility and swelling capacity to form gels. Suitable polymers of this type are available on the market under the names oil Carbopol ® or Polycarbophil ®, for instance from the Goodrich Company. Other suitable polymers of comparable type are disclosed in EP-A-309.404 (included for reference) and comprise copolymers of acrylic acid with allyl ethers of glycols or sugars. Upon addition of water these polymers will form viscous dispersions of microgels which have strong affinity for internal mucous membranes. Furthermore, the gelling and swelling properties of such polymers are pH dependent; hence the volume, bulk and adhesive properties of the carrier can be controlled by adjusting the pH to a desired value.

The present ingestible NMRI contrast compositions are stable even at pH 1 and this is another advantage over similar products of the prior art as they are not attacked by stomach fluids which normally dissolve magnetite particles into $Fe^{+2}$ and $Fe^{+3}$ ions. This is obviously undesirable for both toxicity and imaging efficiency reasons. Bioadhesivity is particularly effective under acid or near neutral conditions; at high pH the bioadhesivity is decreased and may become negligible. Hence control of bioadhesivity by pH control is another asset of the present invention.

For manufacturing the contrast compositions according to the invention one usually admixes the signal generating particles (the echogenic or magnetically responsive particles, or both) with the carrier phase. In regard to the MRI aspect of the invention, one may use magnetic particles which can be ferromagnetic or superparamagnetic. The nature of both and the distinction between them has been stressed before in this specification. Hence, one prefers superparamagnetic particles for opmimalized density efficiency, i.e. magnetic particles of size not exceeding about 150 nm and preferably in the 1–100 nm range (10–1000 A). The preparation of such magnetic particles is well known and disclosed in many references, e.g. the aforementioned references and further references, e.g. U.S. Pat. No. 4,554,088; EP-A-125.995 (Advanced Magnetics); U.S. Pat. No. 4,267,234; U.S. Pat. No. 4,157,323 (California Institute); WO-A-78/00005 (Mosbach); WO-A-83/01738; WO-A-83/03426; WO-A-84/00294 (Schröder). They are also available commercially, e.g. from Ferrofluidics Corp., Burlington, Mass. They normally result from the alkalinization of an aqueous solution containing $Fe^{+2}$ and $Fe^{+3}$ salts in correct proportions.

It has been said that when it is wished to also use the compositions of the invention for ultrasonic echography diagnosis purposes, said compositions will contain echogenic particles, preferably in the form of air- or gas-filled microspheres bounded by a material envelope, e.g. a polymer membrane. The obtention of such echogenic particles is disclosed in many references among which one can cite EP-A-458 745. In this reference, there is disclosed the preparation of microballoons with a soft and resilient membrane envelope which are convenient as echogenic particles in the present invention as they resist pressure variations due to peristaltic movements in the bowels. Notwithstanding, other types of ultrasonic echogenerating particles can be used as well, e.g. those disclosed in the following documents: WO-A-91/12 823, EP-A-327 490, EP-A-324 938.

In one embodiment of a method for preparing the compositions according to the present invention, an aqueous suspension of the magnetic particles is treated with alkali to raise the pH to 13 or more, then the obtained alkaline suspension is admixed with an aqueous solution or dispersion of the carrier phase at the same pH and finally a water-compatible organic solvent in which the carrier phase is insoluble is added, whereby a precipitate of the desired composition is formed. The composition can thereafter be separated, for instance by filtration, and washed free from alkali, then it can be stored dry. When used for internal NMRI investigation, the composition can be rehydrated with water or an aqueous solution of innocuous excipients, this being for oral or enteral administration.

In the foregoing embodiment, the magnetic particles are not covalently linked to the carrier phase, the latter being water-soluble, but still they are immobilized therein presumably due to the existence of electrostatic or Van der Waals forces between the carrier phase constituents and the magnetic parricides or, if the carrier is insoluble in water but in hydrated gel form, to immobilization of the hydrated magnetic particles within the carrier gelled structure.

In another embodiment for preparing the compositions of the invention, the magnetic particles are chemically bonded to the carrier phase by the use of either reactive functions of the carrier itself or of a coupler grafted to the particles, said coupler possessing also functions which will bind to the carrier. For instance, the coupler can be a silane which will bind to the particles by silanation (see EP-A-125.995 incorporated for reference) and which bears a function which may subsequently react with the carrier phase. For example, a useful function of the silane coupler can be an amine group which can further react with negative groups on the carrier material, e.g. COOH or S-OH, sulfate or sulfonate groups, to form ammonium sails. Preferably, if the carrier is an organic polymer obtained by polymerization of one or more monomers, the silane coupler can comprise functions that will copolymerize with said one or more monomers.

Thus for instance, in the case the carrier phase comprises a polymer or copolymer of acrylic acid, this can be prepared by copolymerizing a mixture of acrylic acid (and optionally other olefinic monomers) and magnetic particles carrying grafted thereon silanes with substituents bearing functions copolymerizable with acrylic acid. An appropriate silane for achieving this is trimethoxy-hydroxypropyl acrylate or methacrylate which possesses a double bond copolymerizable with other acrylates. The grafting technique is disclosed for instance in EP-A-113.367 and EP-A-125.995.

For using the present compositions as an echogenic or NMRI contrast agent (or both) in the study of the digestive tract, the compositions (when stored dry) are admixed with an aqueous phase suitable for oral administration in order to provide a gel which will adhere to a predetermined extent to the mucous membrane of the digestive tract and therefore will carry the particles through said tract to the portion thereof to be visualized. The rate of transfer and the transit time can be adapted by properly selecting the nature and degree of bioadhesion of the carrier phase. For this, variable proportions of contrast compositions including water-soluble carrier polymer can be admixed with the bioadhesive carrier, these proportions being selected to reach up to 99% by weight or more in the case where little restricted transit, unrestricted transit or accelerated transit is desired. For instance, for NMR investigations, using mainly dextran as the carrier phase in rats gave a transit rate similar to that observed with no carrier, while using mainly CMC as carrier gave accelerated transit. Using Carbopol® as the carrier phase gave strongly retarded transit, particularly in the duodenum portion of the intestinal tract. The present contrast compositions may also advantageously comprise isoosmolarity agents which minimize loss or gain of water during intestinal transit, i.e. diffusion by osmosis; such agents may comprise carbohydrates such as sorbitol, mannitol, xylitol and the like.

During transit time, the patient having received a dose of the present compositions as NMRI or echogenic contrast agent is subjected to periodical or continuous investigations using conventional echography or NMRI equipment, whereby the obtained processed images can thereafter be used for diagnostic or other medical applications.

BRIEF DESCRIPTION OF THE DRAWINGS

The invention is now illustrated by the following practical examples.

In the drawing:

FIG. 1 refers to the stomach.

FIG. 2, 3, 4, 5 refer to successive parts of the intestine.

EXAMPLES

Example 1

Figure 1:
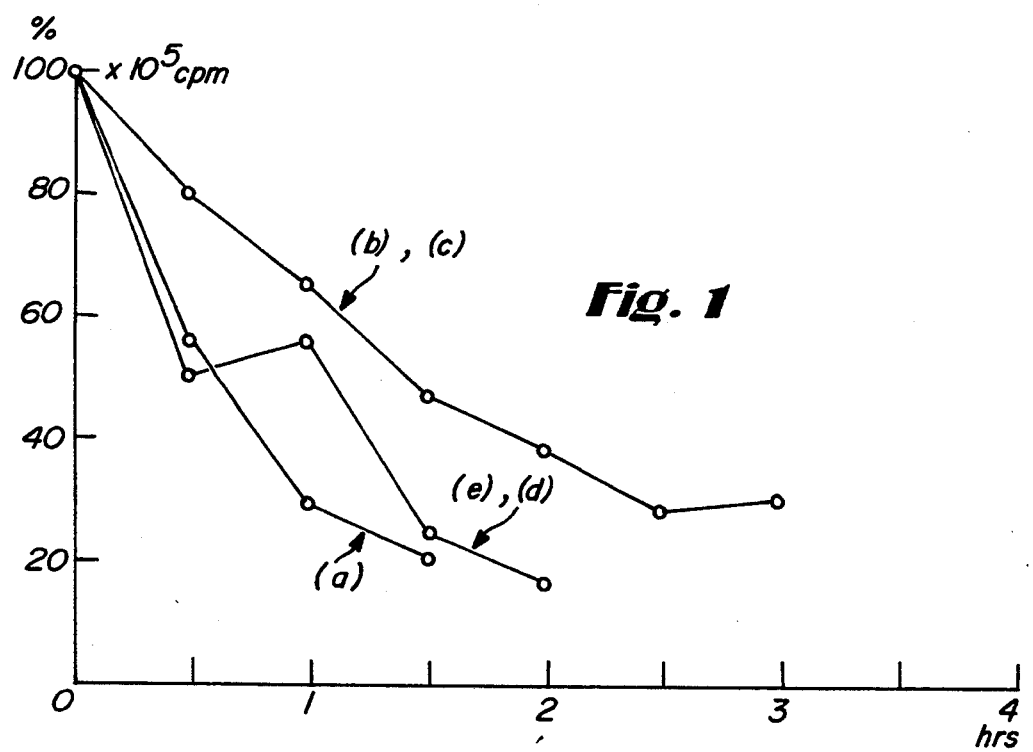
FIG. 1 to 5 illustrate by graph obtained from radioactive tracer measurements the rate of transit (expressed at % radioactivity in function to time) of contrast compositions through the digestive tract of experimental animals.
Figure 2:
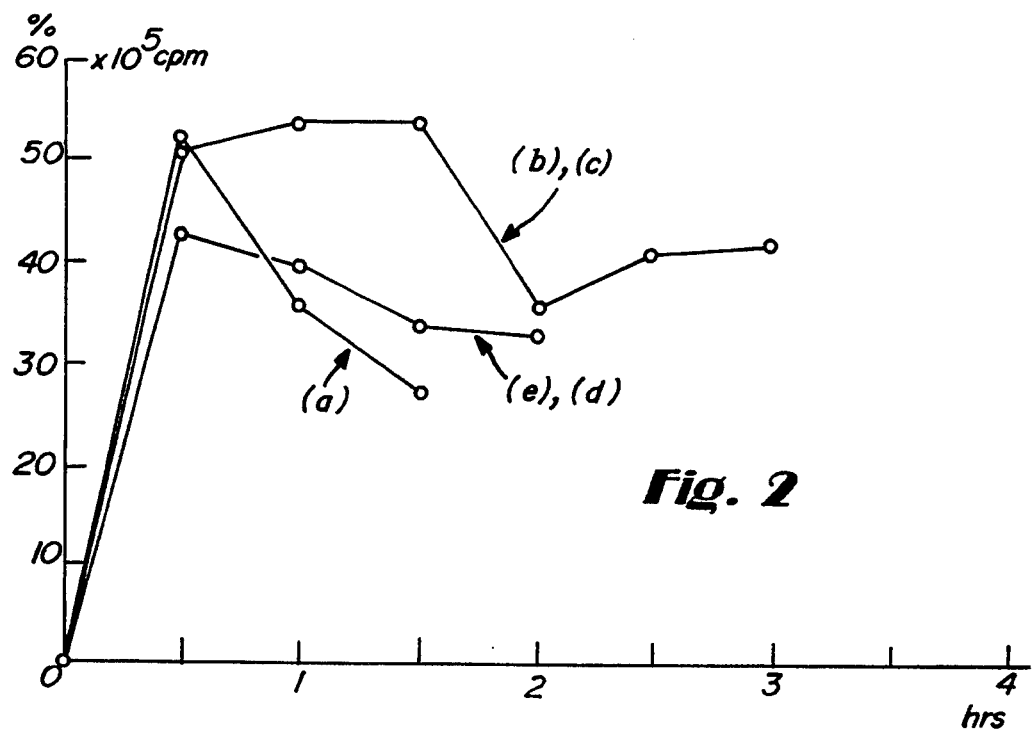
Figure 3:
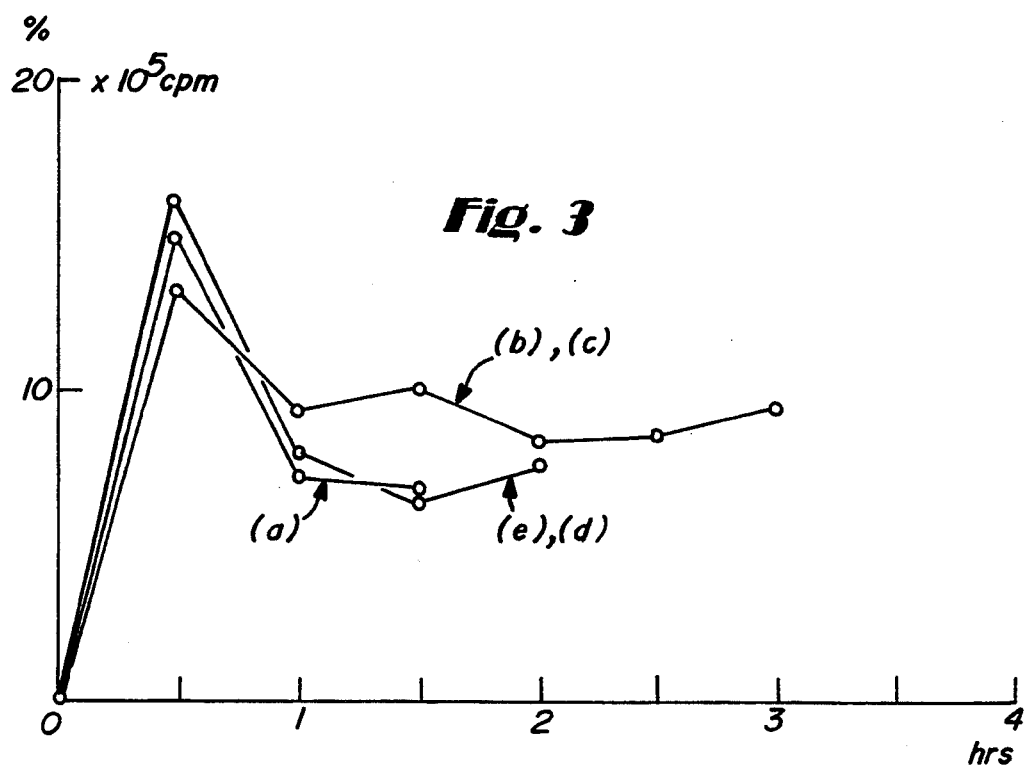
Figure 4:
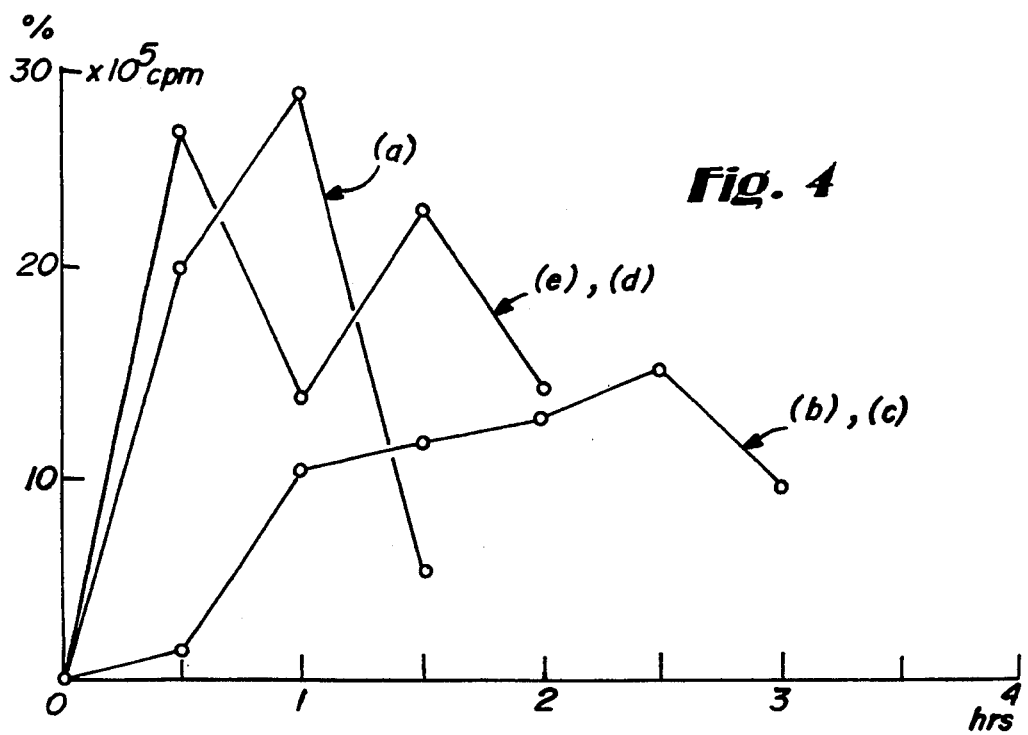
Figure 5:
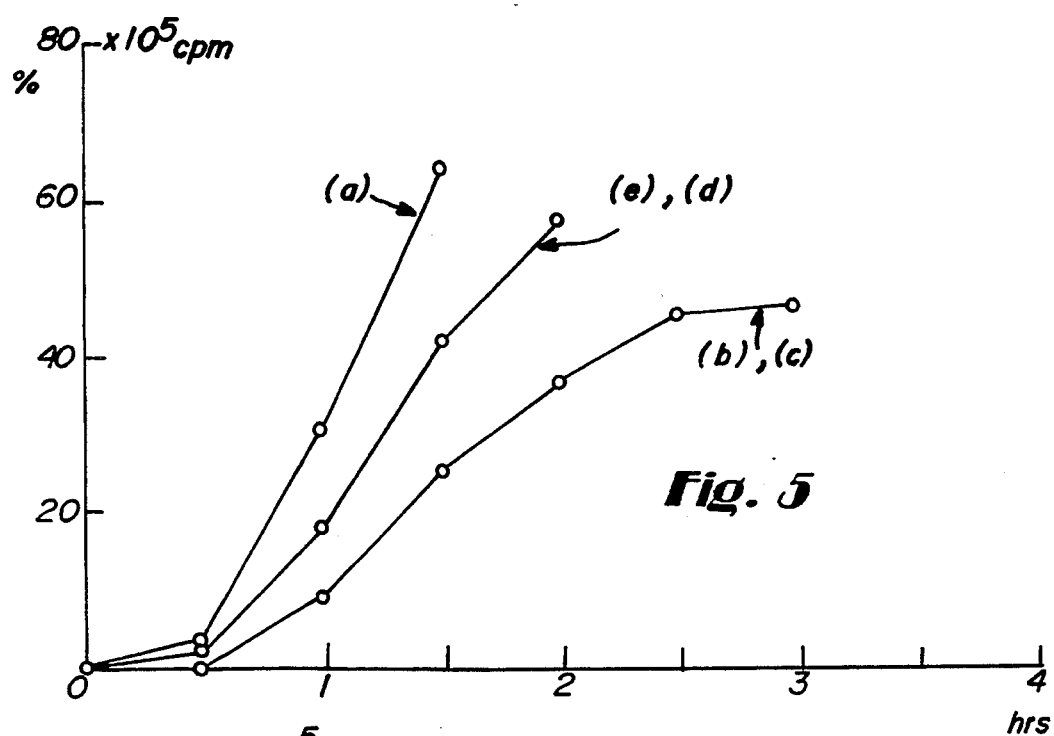

A water solution (30 ml) of $FeCl_3.6H_2O$ (185.3 mg; 0.685 mmol) and $FeCl_2.4H_2O$ (80.5 mg; 0.405 mmol) labeled with $^{59}Fe$ was brought slowly to pH 13.4 by the dropwise addition of 3% aqueous $NH_4$ solution; then it was heated to 75° C. for about 10 min. This resulted in the formation of a dark brown suspension of magnetite in large and coarse particles.

To this was added under agitation a solution of 5 g of Dextran in 200 ml of water and the pH was reajusted to 13.4 by adding some more NaOH solution. After 15 min more stirring, alcohol was added, whereby a very fine precipitate of Dextran-magnetite was formed. This precipitate was drained under suction, washed with alcohol and dried at 50° C. in air.

Radioactive measurements showed that the yield was 94% by comparison with the radioactivity of the initial mixture.

The proton magnetic resonance transverse relaxivity, expressed as $R_2$, i.e. $R_2=1/T_2/\text{mmol Fe}$) was measured on aqueous dispersions of the aforementioned precipitate by means of a 60 MHz RMN spectrometer. The measurements were effected at mid-height of the absorption peaks. Values of $R_2$ in the range of 500–550 $(\text{mM.s})^{-1}$ were obtained which did not substantially change with time, thus showing that reagglomeration of the particles did not occur.

Comparative Tests

A comparative test was performed as disclosed in Example 2 of EP-A-186.616.

To a solution of Dextrin (80 g) in 180 ml of $H_2O$ at 70° C. were added a solution of 19 g of $FeCl_3.6H_2O$ (70 mmol) and 7.01 g $FeCl_2.4H_2O$ (35 mmol) in 105 ml of water. A tracer quantity of $^{59}FeCl_3$ was also added. The pH was raised to 2.4 by first adding 20% aqueous $Na_2CO_3$, then it was brought to pH 11 with 10N NaOH added dropwise, whereby the color of iron oxides developed. The mixture was refluxed for 30 min, then it was cooled to room temperature and the pH was brought to 6.2 with 6N HCl. Then 0.8 liter of ethanol was added which caused the formation of a precipitate. This was collected, resuspended in water and the suspension was dialyzed for 24 hrs in running water (membrane cut-off=10'000). Then the suspension was freeze-dried which gave a blackish powder.

Measurements of $R_2$ as described above gave none or useless responses. Analogous results were obtained by replacing Dextrin by a comparable amount of Dextran. Obviously, the ratio of metal to polymer in this formulation is much too high to prevent reagglomeration of the particles subjected to a magnetic field.

It was also found that when the experiment of Example 1 was repeated, but the magnetite precipitation was effected with the polymer already present in the solution, no useful $R_2$ measurements were obtained.

Example 2

To a solution of 13.56 g $FeCl_3.6H_2O$ (50 mmol) and 5.3 g $FeCl_2.4H_2O$ (27 mmol) in 60 ml of water labeled with $^{59}Fe$ (about $10^6$ cpm) were added dropwise 60 ml of 5M aqueous NaOH until the pH was above 13. The solution was left to stand until a blackish sediment accumulated at the bottom of the container. This was washed carefully by decantation ten times with portions of 300 ml $H_2O$. After the last portions, the pH of the water had dropped to 9.3.

The suspension was acidified to pH 3.2 with glacial $CH_3COOH$ and sonicated for 2 min (Branson Sonifier, output mark 40). Then 10 ml of trimethoxy-3-hydroxypropylsilane methacrylate were added and sonication was resumed for 2 min.

Sixty ml of glycerol were added and the mixture was heated under reduced pressure in a rotavapor until a black viscous residue has formed. This residue was diluted with 240 ml of water, agitated for 20 min and allowed to rest whereby it separated into two phases. This was dialyzed for 24 hrs against a citrate buffer (10 mM, pH 8.3 with ammonia) in order to remove low molecular material (glycerol, unreacted silane and acrylate oligomers).

A suspension was made containing 20 ml of acrylic acid 10 ml $H_2O$ and 10 ml of the silanized magnetite prepared as described above. This suspension was heated to 50° C. and a 10% aqueous ammonium persulfate solution was added dropwise. After the polymerization was complete, the polymer was ground in 500 ml of water and dialyzed against running water. Then it was freeze-dried to give 20.1 g of silvery powder.

A suspension of 1 g of this powder in 100 ml of water was prepared and 1 ml of this suspension was mixed with 9 ml of a 1% aqueous solution of Carbopol R at DH 7–8. The relaxation time $T_2$ was measured as described in Example 1, the value found being $R_2=160$ $(\text{s.mM})^{-1}$.

Example 3

The procedure of Example 1, i.e. the preparation of dispersions of magnetite (1.1 mmol) in aqueous solutions of 5 g of polymer in 200 ml of $H_2O$, was repeated using different polymers according to the Table below.

The Table provides the names of the polymers, the yield of the preparation (calculated on the basis of the iron converted to magnetite) and the relaxivity $R_2$ in terms of $s^{-1}$ mmol $Fe^{-1}/l$.

TABLE

| Polymer | Yield (%) | $R_2$ |
|---|---|---|
| Carbopol | 99 | 601 |
| CMC | 98.6 | 579 |
| Dextran | 93.2 | 539 |
| Na Alginate | 98.2 | 465 |
| Mixture 1:1 Alginate + Carbopol | 95.5 | 605 |

Example 4

In the experiments reported below, magnetite suspensions were prepared as disclosed in Examples 1 and 3, using a tracer amount of $^{59}FeCl_3$ as label. The quantities of iron salts were selected so that the final concentration was about 1.46 mmol of Fe/l. After precipitation with alkali the suspensions were further homogenized by adding a drop of surfactant (Tween-80) and sonication for a few minutes with a Branson sonifier (30 watt output).

Samples of the suspensions (0.1 ml) were diluted with 9.9 ml (dilution 1:100) of 1% by weight aqueous polymer solutions also containing 0.3 mol/l of mannitol to preserve isotonicity. The polymers used were:

a) Carboxymethylcellulose (CMC) Na salt (0.1 g/9.9 ml of water).
b) "Carbosal"; this was the code name given to Carpobol (from the Goodrich Company) when in the form of sodium salt.
c) "SA" polymer; this polymer is disclosed in EP-A-309.404 and is based on acrylic acid copolymerized with a mixture of sucrose mono- and di- allyl ethers with minor quantities of sucrose polyfunctional allyl ether.
d) Dextran.
e) Control; this was made as above by diluting the magnetite preparation to 1/100 but using only water without polymer.

Five ml of samples a) to e) were administered to Sprague-Dawly rats (about 180 g) which were kept fast except for water 24 hrs before administration. The samples were introduced intragastrically with a ball-point syringe. The tracer amount in each sample accounted for about $10^6$ cpm.

At time intervals of 0.5, 1, 1.5, 2, 3 and 6 hrs, animals were sacrificed and stomach, small intestine, caecum and large intestine removed for examination. The small intestine was divided into four segments about equal in length and these were examined separately.

The tests consisted in measuring the radioactive response of the various parts of the digestive tract and correlate the results with time. The global results were that sample (d) (Dextran) behaved about like the control, i.e there was no visible influence of the polymer on the intestinal transit time while (a) accelerated it and (b) and (c) retarded it significantly, thus allowing prolonged examination when visualized under NMRI.

The results are recorded on the graphs of FIG. 1-5 which refer, respectively, to the stomach and to the four successive portions of the small intestine. In the figures, the curves representing control (e) or Dextran (d) (they are practically similar) are marked with full dots; the curves for CMC (a) are marked with empty squares and the curves for the bioadhesive polymers (b) and (c) are marked with shaded squares. These results clearly support the foregoing findings.

If in the experiments reported in this Example the carrier phases were replaced by mixtures of the component carriers, intermediate transit and retention rates were observed. Hence, the compositions of the invention enable to control the length of the periods during which NMRI of the digestive tract portions can be performed.

Example 5

A 3% aqueous solution of $NH_4OH$ (about 25 ml) was slowly added dropwise under agitation to a 100 ml water solution of 619.2 mg of $FeCl_3.6H_2O$ (2.29 mmol) and 262.1 mg of $FeCl_2.4H_2O$ (1.32 mmol). The mixture was then heated to 75° C. for 10 min. There were thereafter added 200 ml of an aqueous 2.5% by weight solution of sodium alginate and the pH was raised to 13.5 with 40% aqueous NaOH. After further agitating for 15 min at room temperature, alcohol was added to precipitate the magnetite-polymer composition; the powder was drained on a filter, washed with alcohol and dried; the yield was 4.96 g containing 0.216 mmol of Fe (theory=0.22 mmol). The mmolar transverse relaxivity $R_2$ was measured at 60 MHz on a water suspension of the powder with a perkin-Elmer/Hitachi NMR apparatus. The measured value was $R_2=465$ $(s.mM)^{-1}$.

Example 6

A 6N aqueous sodium hydroxide solution was added dropwise under agitation to a $^{59}Fe$ labeled aqueous solution of 153.1 mg of $FeCl_3.6H_2O$ (0.566 mmol) and 64.3 mg of $FeCl_2.4H_2O$ (0.323 mmol) until the pH was approximately 12.5; then the mixture was heated to 80° C. and agitated for 10 min at this temperature.

The magnetite suspension was allowed to come back to room temperature, the pH was lowered to 6.5 with 1N HCl and there were added two grams of aluminum-sucrose-octasulfate (sucralfate) sold under the name of Keal ® by Laboratories SINBIO, 75116 Paris (France). The mixture was diluted with 50 ml $H_2O$ and further agitated for 10 min after which it was left to stand, whereby a precipitate of magnetite-sucralfate settled at the bottom of the vessel. This was drained on a filter, washed with water and dried, yield 2.03 g. $R_2$ (in water)$=283$ $(s.mM)^{-1}$.

This powder retained the luminal adhesive properties of the Keal ® product and adhered significantly to selected parts of the digestive tract of experimental animals, whereby satisfactory NMRI of these parts was experienced.

Figure 6:
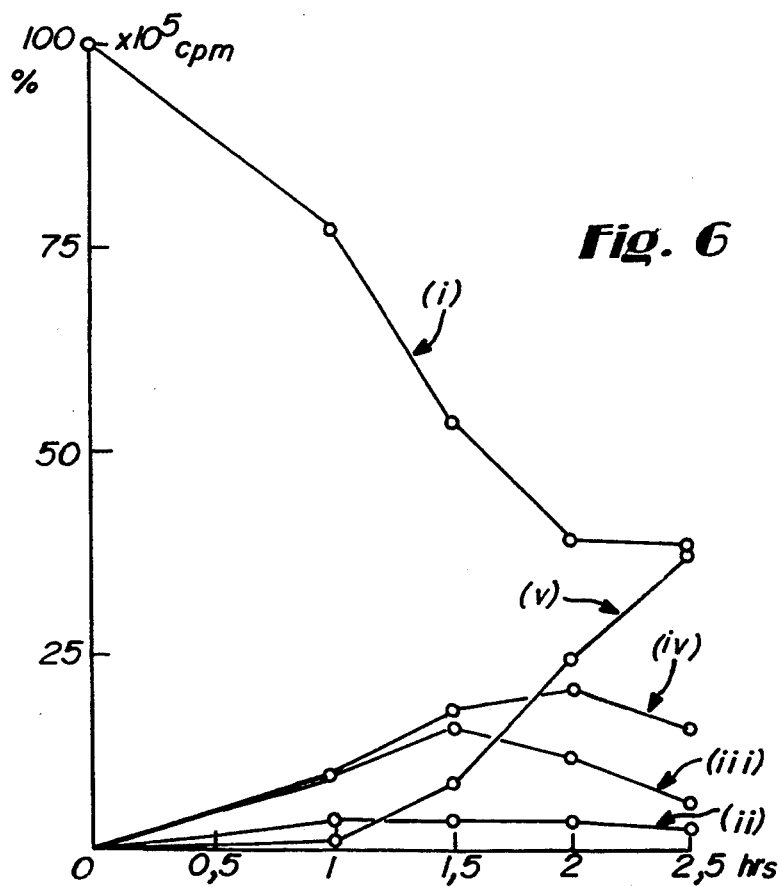
FIG. 6 is a graph illustrating the rate of digestive transit of a sucralfate-magnetite composition according to the invention.

FIG. 6 illustrates the results obtained in which the % residual radioactivity of the tracer is plotted against time for various section of the digestive tract. Curves i to v refer respectively to the following sections:

```
i = stomach
ii = intestine, portion 1
iii = intestine, portion 2
iv = intestive, portion 3
v = intestine, portion 4 + caecum
```

Example 7

Montmorillonite clay of the Beidel type (BEDELIX ®) available from Laboratories Beaufour, 28100 Dreux (France) was tested for NMRI contrast response under the following conditions: three g of BEDELIX ® were stirred in 100 ml of a 0.5% solution of Carbopol ®. The $1/T_2$ value of this preparation was measured as usual with a Perkin-Elmer/Hitachi NMR apparatus at 60 MHz and found to be 435.5 $s^{-1}$ without the addition of magnetite. This value was stable (due to the presence of the Carbopol ®) and the preparation could be used as such for the NMRI of the digestive tract of animals.

However the contrast performances were further enhanced by the incorporation of magnetite as follows:

A suspension of magnetite was prepared as disclosed in Example 1, first paragraph. A 0.2 ml portion of this suspension was added to 99.8 ml of a 0.5% by weight solution of Carbopol ®. The iron concentration in this preparation was 0.178 mmol/ml; the $1/T_2$ value was 144.5 $s^{-1}$, i.e. $R_2=812$ $(s.mM)^{-1}$.

Aliquots of the magnetite preparation were taken and to each were added a different quantity of BEDELIX ®. The $R_2$ values were measured as usual and reported below in function to the % by weight of added BEDELIX ®.

| % of BEDELIX ® | $1/T_2$ $(s^{-1})$ | $R_2$ $(s \cdot mM)^{-1}$ |
|---|---|---|
| 0.5 | 163.4 | 918 |
| 1 | 251.3 | 1412 |
| 1.5 | 402.1 | 2259 |

Example 8

A composition of magnetic particles suspended in aqueous Carbopol ® was prepared as disclosed in Example 4 (item b). The quantities were adjusted to provide a mixture containing about 0.3 μmol of iron (0.0174 mg) per ml and 10 mg/ml of Carbopol ®.

Male Sprague Dawley rats were used for the experiment after 24 hours of fasting. Eight ml of the Carbopol-magnetite solution were administrated orally to the conscious animals which were anesthetized 10 min later by 30 ml/kg of Pentotal. Transversal MR images were then taken on an Esaote ESATOM 5000 imager equipped with a special 8 cm i.d. RF receiver coil, using a slice of 2 mm, a F.O.V. of 15.9×15.9 cm, and a matrix size of 128×256. $T_2$ weighted images (SE 200/70/1), were acquired as well as $T_1$ weighted images (SE 500/16/2), and intermediate scan images (SE 350/50/2). For the T2 weighted and intermediate scan images gradient moment hulling techniques were used in order to minimize respiratory artifacts. The T2 weighted and intermediate scan images show a clear delineation of the darkened and expanded bowel loops. Especially the 350/50/2 image showed very clearly the single loops of the small intestine. The wall of the loops could be clearly observed. A cross section of the colon and of a kidney were also seen as well as abdominal and dorsal muscles. The contrast media was distributed evenly over the whole GI tract.

Example 9

A suspension of echogenic microballoons was prepared as described in Example 4 of reference EP-A-458 745 using poly-L-lactic acid (commercially available under the name of Resomer ® R-207 from Boeringer Ingelheim, Germany). There was obtained a suspension of microballoons in distilled water (concentration $10^9$/ml; average size 5.2 μm).

On the other hand, an aqueous suspension of gelled bioadhesive polymer was prepared by dispersing 1& by weight of Carbopol ® resin (Goodrich Company) in water. The pH of this suspension was brought to 13 with concentrated NaOH and to 100 ml of the alkalinized solution were added 10 ml of the aforementioned microballoon suspension. After homogenizing the mixture under agitation, a quantity of ethanol was added sufficient to precipitate the solids; the polymer was drained on a filter under suction, washed with alcohol and dried under vacuum. The dry powder was then resuspended in 100 ml of a 0.3 M mannitol aqueous solution and the pH adjusted to 3–4 with HCl.

This suspension was used to carry out echographic imaging experiments in-vivo: Laboratory rats were starved for 24 hrs before administration, then they were anesthesized with "Urethane" (1.4 g/kg) and a sample of the contrast suspension was administered intragastrally in 10 sec (6.5 ml/rat). The imaging measurements were effected using an Actson 128-XP/5 apparatus (ACUSON Corp. USA).

Immediately after administration, there was observed a dilatation of the stomach the image of which became entirely white in the two-dimensional imaging mode. In the color Doppler imaging mode, the stomach area showed multiple colors (iridescent yellow-red, blue-green) indicating that the scatterers were in motion. Ten minutes later, imaging of the upper part of the intestine (duodenum) showed a similar colored patterns which indicated that composition containing the reflector microballoons was moving down in the intestinal tract. Expanded bowel loops could be distinguished very clearly and the presence of possible abnomalities could be spotted easily. The spleen was also easily identified.

If in the present example there is used a suspension of microbubbles, for instance that disclosed in WO-A-91/15244, comparable results were noted.

We claim:
1. A method of making an ingestible composition useful as a contrast enhancing agent in the ultrasonic imaging of the digestive tract of humans and animals, said composition consisting essentially of organic microballoons as contrast enhancing particles bound to an organic carrier phase which when hydrated has an adhesive affinity for the gastrointestinal mucosa, said method comprising the steps of:
   selecting a silane coupler having at least two reactive functions:
   grafting said coupler to said microballoons through one of said at least two reactive functions: and
   binding said grafted microballoons to said carrier phase through another of said reactive functions.
2. The method of claim 1, wherein said organic substrate is a polymer of acrylic acid and said coupler is selected such that said another reactive function is co-polymerizable with acrylic acid.
3. The method of claim 1, wherein said organic carrier phase is a copolymer of acrylic acid and another copolymerizable monomer and said coupler is selected such that said another reactive function is copolymerizable with acrylic acid.

* * * * *